US00PP20038P3

(12) United States Plant Patent

Doyle et al.

(10) Patent No.: US PP20,038 P3

(45) Date of Patent: May 26, 2009

(54) FIG TREE NAMED 'SEQUOIA'

(50) Latin Name: *Ficus carica*
Varietal Denomination: Sequoia

(75) Inventors: James Doyle, Pleasant Hill, OR (US); Louise Ferguson, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 148 days.

(21) Appl. No.: 11/643,332

(22) Filed: Dec. 20, 2006

(65) Prior Publication Data

US 2008/0155723 P1 Jun. 26, 2008

(51) Int. Cl.
*A01H 5/00* (2006.01)

(52) U.S. Cl. ..... Plt./211

(58) Field of Classification Search ..... Plt./211
See application file for complete search history.

(56) References Cited

U.S. PATENT DOCUMENTS

| | | | | | |
|---|---|---|---|---|---|
| PP11,325 | P | * | 4/2000 | Nielsen | Plt./211 |
| PP11,347 | P | * | 4/2000 | van Geest | Plt./211 |
| PP12,828 | P2 | * | 8/2002 | Plattner | Plt./211 |
| 2008/0155723 | P1 | * | 6/2008 | Doyle | Plt./211 |

OTHER PUBLICATIONS

The Jan. 22, 2002 Test Agreement For Trees Between Terrestre, Inc. and The Regents Of The University of California. 6 Pages.

The May 1, 2004 Test Agreement For Trees Between Terrestre, Inc. and The Regents Of The University of California. 7 Pages.

The May 1, 2004 Test Agreement For Trees Between V–Tree, Inc. and The Regents Of The University of California. 7 Pages.

The Mar. 1, 2005 Test Agreement For Trees Between DeBenedetto Fruit Company, LLC and The Regents Of The University of California. 6 Pages.

The Mar. 1, 2005 Test Agreement For Trees Between Kevin Herman and The Regents Of The University of California. 6 Pages.

The Jun. 1, 2005 Test Agreement For Trees Between The Fig Company, LLC and The Regents Of The University of California. 6 Pages.

* cited by examiner

*Primary Examiner*—Wendy C. Haas
(74) *Attorney, Agent, or Firm*—Morrison & Foerster LLP

(57) ABSTRACT

A new and distinct variety of Fig tree denominated 'Sequoia' is described. The new 'Sequoia' fig variety is a high quality, medium to large size, yellow-green skinned fig of the "common" type, developed for use in the fresh market fig industry. The 'Sequoia' tree is of medium vigor and size and is a regular and productive bearer, developing both a Breba and second crop in most years. The 'Sequoia' has a tight ostiole that substantially restricts the entry of most insects into the interior of the fig fruit. In comparison with the 'Tena' parent cultivar, the 'Sequoia' is substantially larger in size and has a more prolific Breba crop. The larger size of the 'Sequoia' allows it be harvested later into the fall when the decreased size of other cultivars such as 'Tena' precludes their use in the fresh market.

2 Drawing Sheets

Botanical/commercial classification: (*Ficus carica*)/new fig variety.

Variety denomination: 'Sequoia'.

BACKGROUND OF THE INVENTION

Figs are a popular food item. The new 'Sequoia' cultivar described herein has been developed for the fresh market. The fruit is yellow-green in skin color with reddish-amber pulp. This skin color is competitive with the yellow-green 'Calimyrna' (unpatented), 'Kadota' (unpatented) and 'Sierra' (unpatented) but complementary to the violet-black colored 'CA Brown Turkey' (unpatented) and 'Mission' (unpatented). The 'Sequoia' is a common type fig. This gives it an advantage over the 'Smyrna' (unpatented) type 'Calimyrna' in productivity and production efficiency. The Breba crop of 'Sequoia' ranges from light to medium in volume. The Brebas are large in size with very good quality. The production of commercial Brebas gives the 'Sequoia' an advantage over the 'Calimyrna', 'CA Brown Turkey' and 'Sierra' cultivars that either develop very few or no Brebas at all. The second crop of 'Sequoia' is abundant with large to medium size. The 'Sequoia' appears to maintain fruit size well into the fall in contrast to the small late-season fruit size of the 'Mission' and 'Kadota' and the absence of fruit on the 'Calimyrna'. The ostiole or eye of the 'Sequoia' is very tight, similar to the 'Sierra' and 'Mission' but substantially tighter than the 'Calimyrna', 'CA Brown Turkey' and 'Kadota'. The fruit flavor and quality of the 'Sequoia' is as good as or better than all of the five established cultivars listed here with the exception of the 'Calimyrna'. The 'Sequoia', which has 'Calimyrna' in its pedigree, approaches the flavor of 'Calimyrna', but the 'Calimyrna', with all of its many production problems, still retains its position as the premier quality fig.

SUMMARY OF THE INVENTION

The new 'Sequoia' fig variety can be characterized as a high quality, medium to large size, yellow-green skinned fig of the "common" type, developed for use in the fresh market fig industry. The 'Sequoia' tree is of medium vigor and size and is a regular and productive bearer, developing both a Breba and second crop in most years. The 'Sequoia' has a tight ostiole that substantially restricts the entry of most insects into the interior of the fig fruit. In comparison with the 'Tena' (unpatented) parent cultivar, the 'Sequoia' is substantially larger in size and has a more prolific Breba crop. The larger size of the second crop 'Sequoia' fruit allows it to be harvested later into the fall when the decreased size of other cultivars such as 'Tena' precludes their use in the fresh market.

The new fig selection 'Sequoia' is the result of a controlled cross, performed in June of 1992. The hybridization site was located in a small planting of collected fig cultivars growing near the town of Clovis in Fresno County, Calif. The cross was made between the commercial cultivar 'Tena' as the female (seed) parent and pollen from a proprietary caprifig (unpatented) identified as 'D3-11' as the male parent. The 'Tena' fruit was covered with a cloth organdy sleeve cage well in advance of fruit receptivity, in order to exclude any insects that might enter the fig fruit and effect unwanted pollination. At the receptive stage, the cage was removed from the developing 'Tena' fruit, after which pollen from the 'D3-11' was introduced into the interior of the fruit. The sleeve cage was then replaced over the fruit and remained in place until the fruit matured.

Hybrid seed was extracted from the mature dried fruit in fall of 1992. The seed was then planted in small growing containers in a greenhouse in Parlier, Fresno County, Calif. in early spring of 1993. By late spring of 1993, the developing seedlings were transplanted into seedling rows in the field in Parlier. A total of 918 hybrid fig seedlings were planted in 1993, 353 of which were from the 'Tena' by 'D3-11' cross. From among the seedlings in this population, the seedling identified as 'Sequoia' first fruited and was first selected in September of 1998.

The first propagation of the 'Sequoia' selection occurred in spring of 2001 in a fig selection block in Parlier. The selection was grafted onto an existing fig tree (*Ficus carica*) that was 4 years of age at that time. The 'Sequoia' produced a few fruit the following year in September of 2002, and produced a normal crop of fruit in 2003, 2004, 2005 and 2006. The characteristics of the propagated tree are identical in all aspects of fruit and vegetation to the original seedling. The name 'Sequoia' has been given to this new cultivar.

BOTANICAL DESCRIPTION OF THE PLANT

Figure 1:
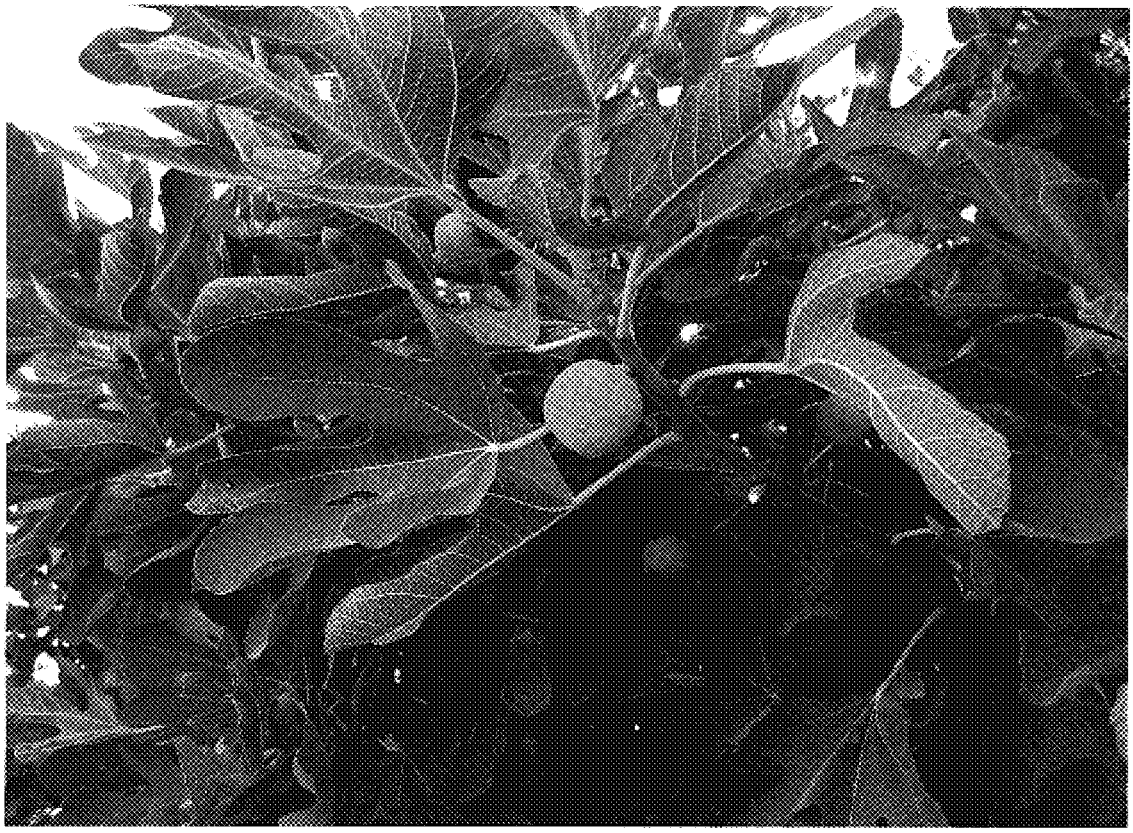
FIG. 1 shows 'Sequoia' second (main) crop fruit, displaying typical fruit color at maturity and the distinctive tight fruit ostiole.
Figure 2:
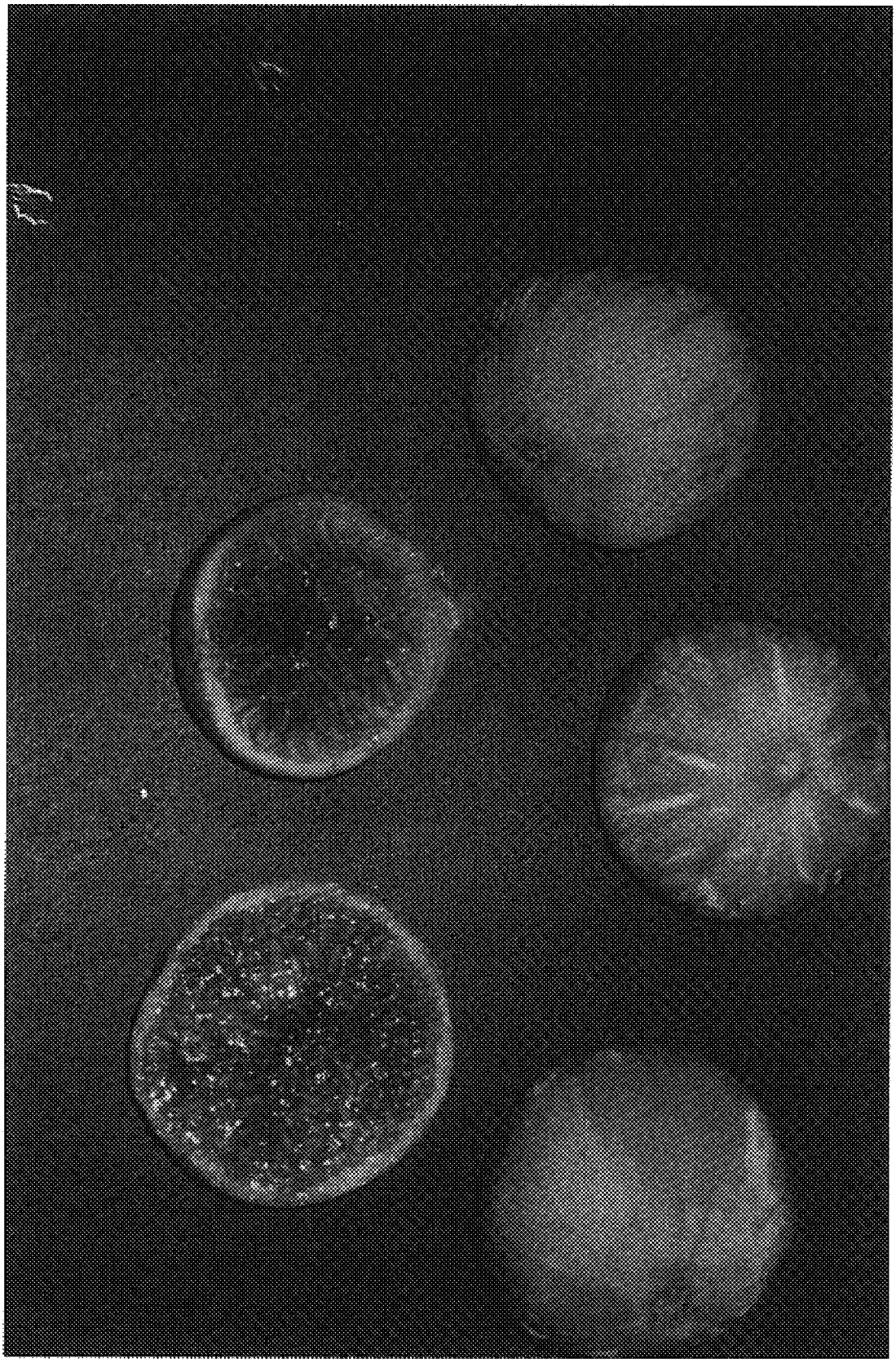
FIG. 2 shows 'Sequoia' fig fruit.

The following plant description was prepared during the 2005 growing season. Plant material and fruit of the new cultivar were obtained from the original first propagated tree in the fig selection block located, in Parlier, Fresno County, Calif. Age of the rootstock fig in 2005 was approximately ten years. Age of the 'Sequoia' grafts on the stock was approximately five years. Color definitions used in this description are from "The Royal Horticultural Society Colour Chart", 3$^{rd}$ edition published at London, England in 1995.

Tree: The genus and species of the new cultivar is *Ficus carica.* Tree vigor is medium for the species. Tree size is medium and the new cultivar is hardy under the typical climatic conditions found in the San Joaquin Valley of California. Tree form is upright to upright-spreading and the tree has been trained to a general open vase type pruning system. The tree is relatively dense and round-topped. Tree size near the end of the 2005 growing season ranged from 4.3 to 4.4 meters in height, including from 1.8 to 2.0 meters of new growth in the top of the tree. Tree width ranged from 4.9 to 5.2 meters in diameter. The subject tree was propagated by grafting onto an existing fig (*Ficus carica*) tree that was 4 years of age at the time of grafting. Most commercial figs are propagated by cuttings and grown on their own root. It is not uncommon, however, for commercial orchards to be grafted when the grower wishes to change to a different cultivar. The original orchard spacing in the fig selection block was approximately 5.5 by 5.5 meters (18 by 18 feet), although many trees are now missing in this planting due to the discarding of unsuccessful selections. The 'Sequoia' selection is of the "common" fig type, that is, it does not need to be caprified (pollinated) to produce fruit. The tree is productive and a regular bearer.

Trunk and scaffolds: The tree trunk is made up of the rootstock, which, at about 80 cm from the ground surface was topworked with five graftsticks of the new cultivar. The basal diameters of the five grafts currently range from 8.0 to 13.0 cm in diameter. These five grafts are formed into the primary scaffolds of the vase-shaped tree. Length between nodes on these scaffolds ranges from 5.1 to 9.4 cm. Scaffold surfaces are relatively smooth with only very slight netting on the surface. A few bark tubers are present, generally globose in form and measuring from 1.0 to 2.5 cm in diameter. There is some slight ridging at each node, extending around the circumference of the scaffold. Scaffold bark color is grayish (Fan #4, Sheet 197-C). Numerous small and relatively obscure lenticels are present over the scaffold bark surface. These lenticels are usually oval in form, flattened horizontally, and range from 1.0 to 2.0 mm in width and from 0.5 to 1.0 mm in height. The lenticel surface color is brownish (Fan #4, Sheet 165-C).

Branches: Branch size for this new cultivar is generally average for the species. The bases of secondary branches that arise off of the scaffolds, range from 4.2 to 4.8 cm in diameter, with internodal lengths ranging from 4.1 to 4.8 cm. These secondaries are grayish in color (Fan #4, Sheet 197-C) with relatively smooth surfaces. Smaller, often horizontal branches arising off of secondaries can range from 2.7 to 3.2 cm in diameter at their bases, with internodal lengths from 5.1 to 7.0 cm. Much of this wood is current season growth, with the less mature parts a medium green color (Fan #3, Sheet 148-A) and the more mature parts a darker green (Fan #3, Sheet 146-C). The smallest bearing branches, mostly current season growth, range from 0.8 to 1.3 cm in diameter at the base with relatively smooth surfaces. Internode length ranges from 3.1 to 6.2 cm. These small branches can be pale green in color (Fan #3, Sheet 138-C) or a darker green (Fan #3, Sheet 148-A).

Branch bud tip: The bud tip position can be variable but most frequently is oblique to the vertical. Bud tip color is a light green (Fan #3, Sheet 144-D).

Leaves: Leaves are generally large in size with normal thickness. Leaf measurements have been obtained from leaves growing at or below mid-shoot on vertical, vigorous, current season growth. The leaves vary from 26.5 to 30.9 cm in width and from 26.2 to 34.2 cm in length, not including the petiole.

Leaf form: There is some variability throughout the tree. Most frequently, the leaves are palmately lobed with five lobes present. The lobes are usually spatulate in form, but some variation does occur. The leaf base usually is calcarate in form but some cordate forms can occasionally occur. The leaves are highly pubescent on both the upper and lower surfaces, with dense and short pubescence. The leaf sinuses are of medium depth. The sinus bottoms are variable but most frequently are U-shaped in form. The leaf veins are relatively prominent, especially on the lower leaf surface. Both the upper and lower leaf vein surfaces are pubescent.

Leaf color: Color of the upper leaf surface is a dark green (Fan #3, Sheet 137-B). Color of the lower leaf surface is a lighter grey-green (Fan #3, Sheet 138-B). Leaf vein color is a pale green-yellow (Fan #3, Sheet 145-C). The leaf surfaces are slightly dull in color.

Leaf margins: The leaf margins are most frequently crenate with very low crenations. The crenations are usually most prevalent on the outer margins of the lobes, with the inner lobe margins often nearly linear.

Leaf petiole: Leaf petioles range in size from 12.2 to 13.5 cm in length and from 0.5 to 0.7 cm in basal thickness. Petiole color is a pale green-yellow, either (Fan #3, Sheet 145-B) or (Fan #3, Sheet 145-C).

Fruit description: The following descriptions are of both the first and second crop of the new 'Sequoia' fig cultivar. The first crop, known in the fig industry as the "Breba" crop, is borne on the previous season's growth. The first crop is usually relatively light in volume, has large fruit size and begins to mature in early June. The second crop is borne on current season's growth and is also sometimes referred to as the "main" crop. This second crop is usually abundant in volume, has somewhat smaller fruit size than the first crop and begins to mature in early August. A detailed description of each crop follows.

Breba (First) Crop of Fig Selection 'Sequoia'

Maturity: Fruit of the Breba crop of 'Sequoia' begins to mature approximately in the first week of June (June $7^{th}$ in 2005) in the Central San Joaquin Valley of California. Harvest of this first crop would usually be completed within about two to three weeks of its inception. The fruit is described at full commercial maturity. The Breba crop is moderate light in comparison with the main crop but, in most years, would probably be economically feasible to pick.

Fruit size: The fruit is large in size, ranging from 48 to 64 mm in diameter and from 96 to 104 mm in length, including the neck and stalk. Individual fruit weight can range from 51 grams up to as much as 110 grams, with many fruit in the 80 to 90 gram range.

Fruit form: The fruit form is oblique-pyriform with a relatively prominent and thick neck. The neck at times is flattened laterally.

Fruit stalk: The fruit stalk is short, from 3.0 to 5.0 mm in length and from 5.0 to 7.0 mm in thickness. Stalk color is light yellow-green (Fan #3, Sheet 145-A). The stalk is pubescent. Three bracts are present at the apex of the stalk, where the stalk adjoins the fruit neck. These bracts are rather broad and somewhat conic in shape, from 4.0 to 5.0 mm in width and from 3.0 to 4.0 mm in height. The bracts are appressed to the neck of the fruit. Bract color is a light green-yellow (Fan #3, Sheet 145-A).

Fruit ribs: Longitudinal ribbing is present on the fruit surface. The individual fruit ribs are continuous from the ostiole to the basal shoulder of the fruit body. The ribs are moderately narrow and only slightly elevated. The rib color is slightly darker than the general skin color and can be a medium green (Fan #3, Sheet 144-B) or a darker green (Fan #3, Sheet 146-C).

Fruit ostiole: The fruit ostiole (or eye) is small and relatively tight, affording good resistance to entry of the fruit by insects. Ostiole diameter can range from 1.0 to 2.0 mm in diameter. External ostiole scale color is pinkish and slightly translucent as the fruit approaches commercial maturity (Fan #4, Sheet 179-D). The scales become more brownish in color as the fruit approaches tree-ripe maturity (Fan #4, Sheet 165-D). The ostiole scales are medium to large in size, from 3.0 to 4.0 mm in width and from 2.0 to 2.5 mm in height. The scales are conic in form.

Fruit skin: The fruit skin is medium to slightly thin in thickness, becoming more fragile as the fruit advances in maturity. The skin is moderately glossy with light, waxy bloom present. Longitudinal skin cracking can occur on some fruit as it becomes tree ripe. The skin peels easily from the fruit at full maturity.

Skin flecking: Numerous white flecks (Fan #4, Sheet 155-C) are scattered over the skin surfaces, most prevalent over the body of the fruit. The flecks are usually somewhat oval in form and in a range of 0.5 to 3.0 mm in length and 0.5 to 1.0 mm in width.

Skin color: At commercial maturity, the fruit skin is a light green-yellow (Fan #3, Sheet 144-C) or a slightly darker green (Fan #3, Sheet 144-D). Some fruit can display a bronze coloration on part of the fruit surface (Fan #3, Sheet 152-C), especially fruit that is more exposed on the periphery of the tree. In cool years, the bronzed areas can darken to a brown (Fan #4, Sheet 176-C) that most frequently occurs on the apical half of the fruit.

Fig meat: The color of the fig meat is white (Fan #4, Sheet 155-A). The meat is firm and relatively thick, especially in the interior area just below the fruit neck. Lateral meat thickness ranges from 3.0 to 7.0 mm.

Fig pulp: The fig pulp is amber to a light strawberry red in color, from (Fan #4, Sheet 173-B) to (Fan #1, Sheet 34-C). The fig syconium is nearly filled with the fine-textured pulp, leaving only a small, unfilled cavity in the center of the fruit.

Seeds: The fig seeds are small in size and abundant. Uncaprified fig seeds (cenocarps) are usually hollow, without an internal embryo. Seed color is a light tan-brown (Fan #4, Sheet 161-A).

Fig flavor: Flavor of the Breba crop is very good. The fruit is sweet and rich. Flavor of the Breba crop can be variable, with the best quality attained where spring and early summer temperatures are high.

Suitability: Fruit of the Breba crop of 'Sequoia' is most suited for use in the fresh market.

Second (Main) Crop of Fig Selection 'Sequoia'

Maturity: Fruit of the second crop of the 'Sequoia' fig selection begins to mature in early August (approximately 5 August in 2005) in the Central San Joaquin Valley of California. Once harvest begins, figs are produced successively in the axils of actively growing shoots throughout the late summer and fall. The commercial production of fig fruit terminates either when the shoot stops elongating and fruit stops forming (usually because the orchard dries out) or when a weather event (rain, frost, fog, etc.) damages the marketability of the fruit. The fruit below is described at full commercial maturity.

Fruit size: The fruit is medium to large in size and abundant. The 'Sequoia' tree is of the "common" or "persistent" type, that is, it does not need to be pollinated (caprified) in order to set fruit. The fruit varies from 53 to 69 mm in length, including the neck and stalk, and from 51 to 55 mm in diameter. Fruit weight varies from 45 to 66 grams.

Fruit form: The fruit form can be somewhat variable. Most frequently, the fruit body is oblate with a prominent neck. At times the fruit body can be somewhat pyriform, also with a prominent neck. The neck is relatively thick, elongated and often curved.

Fruit stalk: The fruit stalk is short, from 4.0 to 6.0 mm in length and from 5.0 to 6.0 mm in thickness. The stalk is usually not swollen. The stalk surface is pubescent with a short, fine pubescence. Stalk color is a pale green (Fan #3, Sheet 144-D). Three stalk bracts are present at the apex of the stalk, where the stalk adjoins the fruit neck. The bracts are relatively large, somewhat triangular in form and not tightly appressed to the stalk. The bract color is a yellow-green (Fan #3, Sheet 145-B).

Fruit ribs: Ribbing is present uniformly on the surface of the fruit, running longitudinally from fruit base to apex. The ribs are not prominent and are relatively smooth. At commercial maturity, the ribs are slightly greener (Fan #3, Sheet 149-C) than the surrounding fruit surface.

Fruit ostiole: The fruit ostiole is small and very tight, with from 0.0 to 1.0 mm opening diameter between the surrounding rows of scales. The scales are somewhat conical in form, ranging from 1.0 to 1.5 mm in height and from 2.0 to 2.5 mm in width at the base of the scale. The scale color is variable, most frequently a pale yellow-green (Fan #3, Sheet 150-B), about the same color as the main body of the fig. At times, the scales can have a pinkish hue (Fan #4, Sheet 179-D), becoming darker and more brownish as the fruit becomes tree ripe (Fan #4, Sheet 165-D). The scales lay relatively flat at maturity. Often, a greenish ring (Fan #3, Sheet 144-C) is present, circling the eye of the fruit.

Fruit skin: The fruit skin is of medium thickness and durability. The skin surface is not very glossy, with a light, waxy bloom. The skin peels readily from the fruit at full maturity. Some skin checking can be present on a low percentage of fruit at commercial maturity. Usually, but not always, the checking is in a longitudinal direction. The skin surface is lightly pubescent with fine, short and somewhat scattered pubescence present.

Skin flecking: The fruit skin is moderately flecked with white colored flecks (Fan #4, Sheet 157-B) scattered over the skin surface. The flecks can range from 0.5 to 2.5 mm in height and from 0.5 to 1.5 mm in width. The flecks are roughly oval, longer in the longitudinal plane.

Skin color: The skin is a yellow-green at commercial maturity (Fan #3, Sheet 150-B), becoming more yellow at full ripe maturity (Fan #3, Sheet 151-C).

Fig meat: The interior meat, located just under the skin, is firm and ranges from 3.0 to 6.0 mm in thickness both laterally and near the apical end of the fruit. The meat at the basal (stem) end of the fruit is much thicker, ranging from 5.0 as much as 15.0 mm in thickness. Meat color is white (Fan #4, Sheet 155-A).

Fig pulp: The fig pulp usually fills the syconium completely to the center. At the center, a broad horizontal interface is present where the upper and lower pulp surfaces meet. The pulp color is a light strawberry red (Fan #1, Sheet 39-A). Pulp texture is relatively fine-grained.

Seeds: Numerous small seeds are present in the fig pulp. These seeds average about 1.5 mm in diameter and vary from globose to oval in form. Seed color is a light tan (Fan #4, Sheet 164-C). Uncaprified (unpollinated) fig seeds, or cenocarps, are usually hollow and have no embryo present within the shell of the cenocarp.

Fig flavor: Flavor of the new fig cultivar is very good, both sweet and moderately rich. The fig also has a mild but distinctive, pleasant aroma.

Suitability: Fruit of the second crop of the 'Sequoia' cultivar is primarily suited for use in the fresh market. The mature fruit dries well, with good dried flavor but the dried fruit darkens in both pulp color and skin color, limiting its value to the dried fruit industry.

Floral Biology

Many tiny, pedicellate fig flowers develop within each fig syconium as figs initiate along the growing shoot throughout the season. These flowers become receptive when each developing syconium is only about 1 to 2 cm in diameter. The florets have a five-part perianth and are unisexual, with long-styled pistillate flowers. Several types of figs have been identified pomologically and the 'Sequoia' falls into the "common" or "persistent" category. This signifies that the fig does not need to be pollinated (or caprified) in order to set and mature fruit.

Comparisons

A "2002 Statistical Review" published by the California Fig Advisory Board and California Fig Institute at Fresno lists seven cultivars used primarily (although in some cases not exclusively) for dried whole figs and fig paste. These seven cultivars are 'Calimyrna' (6,559 acres), a four cultivar grouping identified as 'Adriatics' (unpatented) but including 'Conadria' (unpatented), 'Adriatic', 'Di Redo' (unpatented) and 'Tena' (3,364 acres in combination), 'Kadota' (1105 acres) and 'Mission' (3702 acres). Two additional cultivars are used in California primarily for the fresh market. These are the 'California Brown Turkey' (about 2000 acres) and a 2005 University of California release, the 'Sierra' fig (about 200 acres). The above nine cultivars differ substantially from one another in aspects of suitability, horticultural type and fruit characteristics. The 'Sequoia' fig is being released for use in the fresh market. Although of good quality when dried, it develops both a dark skin and a dark pulp color that limits its acceptability as a dried product. Of the above nine cultivars, only five are sold fresh. These are the 'CA Brown Turkey', 'Sierra', 'Calimyrna', 'Mission' and 'Kadota'. Only these five will be compared, as follows, to the 'Sequoia'. The four 'Adriatic' class figs are used only as whole dried figs or fig paste. All are of too small a size for the fresh market.

Horticultural Types

Two horticultural types of figs are found in the California industry. The first of these, the 'Smyrna' type fig, needs to be pollinated (caprified) in order to set fruit that will persist on the tree until maturity. The 'Calimyrna' is the only cultivar of this type grown commercially for fresh consumption in California. All of the other four fresh market figs listed above, as well as the 'Sequoia', are of the "common" type. These common types do not need to be pollinated in order to set and mature fruit. The advantages of the common type figs over the 'Smyrna' type are substantial. A common type fig grower does not need to maintain caprifig trees or to buy caprifigs from other growers, does not need to treat the caprifigs to disinfect the wasps (the pollen vectors) living in the caprifigs, does not need to distribute the caprifigs throughout the 'Calimyrna' orchard and does not have to deal with the variables or the costs of the caprification process. Climatic factors such as heat, cold, rain, wind and disease can have a substantial impact on the success of the insect vector of the pollen and the eventual level of productivity of the 'Calimyrna' crop. A good 'Calimyrna' orchard often produces only in the 0.5 to 1.0 ton of dried fruit range in comparison to at least twice (sometimes three times) that tonnage from common types. Were it not for the excellent quality of the 'Calimyrna' product, when well grown, it would probably not be planted in California at all.

Usage

The 'CA Brown Turkey' is grown almost exclusively for the fresh market. It does not dry well. The 'Calimyrna', 'Mission' and 'Sierra' are dual-purpose figs, all three dry well, with some growers often directing part of the crop to the fresh market. The 'Kadota' is a multiple use cultivar that can be dried, canned and picked for the fresh market successfully.

Fruit Characteristics of the Five Fresh Market Figs Grown in California

The 'Calimyrna' fig is a green-yellow to yellow skinned fig with amber pulp. As noted above, the cultivar requires caprification to set a crop. The first (Breba) crop drops without coming to maturity because caprifigs containing pollen and the vector wasp are not available at the time the 'Calimyrna' Brebas require pollination. The second crop is abundant but of limited duration (from late August to late September in Fresno County). Fruit set coincides with the midsummer (or profichi) flight of the fig wasp. When the flight is complete, no more fruit is set for that season. Early in maturity of the second crop, fruit size is large, although size can drop off in late September. The size of the 'Calimyrna' fruit eye (or ostiole) is the largest of all the commercial cultivars and can range from 2.2 to 3.5 mm, allowing substantial amounts of internal insect infestation and spoilage. The cultivar is also prone to large numbers of eye splits during periods of high humidity, cool weather or rain. Fruit quality, when the fruit is grown well, sets the standard for excellence.

The 'California Brown Turkey' is a purple-violet colored fruit with areas of yellow to yellow-green visible, especially over the fruit neck and near the fruit stem. Pulp color is a strawberry red. This cultivar is of the common type, not needing caprification. The 'CA Brown Turkey' can set a small crop of large sized first crop (Breba) fruit. As grown in California, however, the tree is severely pruned in the winter to keep it short in height and to facilitate hand harvesting of the large second crop from the ground. This pruning essentially eliminates the first crop. The second crop is abundant and the fruit is large and retains its large size well into the harvest season. Since the 'CA Brown Turkey' is a common type fig, once fruit production begins in late August, fruit will continue to develop and mature until fall. Production ceases only when the orchard dries out and the tree stops producing extension growth, or when a weather event (rain, frost, etc. . . . ) damages the fruit or sends the tree into dormancy. The fruit ostiole is relatively large and in some locations the fruit can be subject to insect infestation and souring. Fruit quality is good when harvested with sufficient maturity.

The 'Mission' fig is a violet-black colored fig with the coloration usually covering the entire fruit surface. Pulp color is a strawberry red. This cultivar is a common type fig not needing caprification. The cultivar usually sets a good crop of Breba fruit that are large in size and of very good quality. These 'Mission' Brebas are often harvested from orchards that have been established to produce fruit for drying. Such trees are often very large and picking can be difficult and expensive. The 'Mission' second crop is abundant and also of very good quality. Fruit size of the second crop is large enough to pack fresh for a week or two, but then size diminishes rapidly, eliminating its use for the fresh market. The fruit ostiole of both the Breba and second crop is quite small and fruit spoilage is usually not a problem. Fruit quality of both crops is very good.

The 'Kadota' fig is a medium sized greenish-yellow skinned fruit that is grown only in limited quantity for the California fresh market. Pulp color is amber. The 'Kadota' is a common type fig. Production of a Breba crop can be variable, from light to good in volume. The second crop is abundant but most fruit is too small to be valuable for picking fresh. Towards the end of the season many small, dry, commercially worthless fruit, known as "puffballs", can be present. The fruit ostiole is medium in size, partially restricting insect access. Fruit quality of the Brebas and second crop is sweet and good.

The 'Sierra' fig is a cultivar, released for planting to California growers by the University of California in 2005. Although developed as a high quality fig for drying, initial plantings are being made for the fresh market so that the new cultivar appears to be suitable for both purposes. Skin color of the 'Sierra' is a yellow-green and pulp color is amber. The 'Sierra' is a common type fig. The Breba crop of 'Sierra' to date does not appear to have commercial value. The Breba crop has been light and the figs produced have not been particularly large or highly flavored. The second crop, however, is abundant. The fruit is medium to large in size and holds fruit size well into the fall. The fruit ostiole is very tight, effectively restricting insect access to the fruit interior. Fruit flavor is very good.

'Sequoia' Comparison

The new 'Sequoia' cultivar described herein has been developed for the fresh market. The second or main crop fruit is yellow-green in skin color with reddish-amber pulp. This skin color is competitive with the yellow-green 'Calimyrna', 'Kadota' and 'Sierra' but complementary to the violet-black colored 'CA Brown Turkey' and 'Mission'. The 'Sequoia' is a common type fig. This gives it an advantage over the 'Smyrna' type 'Calimyrna' in productivity and production efficiency, as well as in the duration of cropping in any one season. Harvest of the 'Sequoia' will extend substantially longer into the fall then 'Calimyrna' harvest. The small ostiole of 'Sequoia' and the absence of the fig wasp, required for set of 'Calimyrna' fruit, allows for lowered insect and disease infestation in the 'Sequoia' fruit in comparison to 'Calimyrna', resulting in the production of greater numbers of merchantable figs. The Breba crop of 'Sequoia' ranges from light to medium in volume. The Brebas are large in size with very good quality. The production of commercial Brebas gives the 'Sequoia' an advantage over the 'Calimyrna', 'CA Brown Turkey' and 'Sierra' cultivars that either develop very few or no Brebas at all. The greenish to green-bronze colored Brebas of the 'Sequoia' will offer a color, size and type of fig that is not presently found in commercial markets. The second crop of 'Sequoia' is abundant with large to medium size. The 'Sequoia' appears to maintain fruit size well into the fall in contrast to the small late-season fruit size of the 'Mission' and 'Kadota'. The ostiole or eye of the 'Sequoia' is very tight, similar to the 'Sierra' and 'Mission' but tighter than the 'CA Brown Turkey' and 'Kadota'. The fruit flavor and quality of the 'Sequoia' is as good as or better than all of the five established cultivars listed here with the exception of the 'Calimyrna'. The 'Sequoia', which has 'Calimyrna' in its pedigree, approaches the flavor of 'Calimyrna', but the 'Calimyrna', with all of its many production problems, still retains its position as the premier quality fig. Trees of the 'Sequoia' are moderate in size, substantially lower in vigor than the 'Sierra' cultivar that is the 'Sequoia's' most likely competitor. The smaller size of the 'Sequoia' tree will enable lower picking costs in comparison to the eventual harvest costs associated with the large vigorous 'Sierra' tree.

What we claim is:

1. A new and distinct variety of fig tree substantially as shown and described herein.

* * * * *